United States Patent [19]
Luebke et al.

[11] Patent Number: 5,300,696
[45] Date of Patent: Apr. 5, 1994

[54] C4 REJECTION FOR ETHERIFICATION AND ISOMERIZATION PROCESS

[75] Inventors: Charles P. Luebke, Mount Prospect; Srikantiah Raghuram, Buffalo Grove; Joseph E. Zimmermann, Arlington Heights, all of Ill.

[73] Assignee: UOP, Des Plaines, Ill.

[21] Appl. No.: 998,177

[22] Filed: Dec. 29, 1992

[51] Int. Cl.$^5$ .................. C07C 41/06; C07C 5/22
[52] U.S. Cl. ..................... 568/697; 585/310; 585/314
[58] Field of Search .............. 568/697; 585/310, 314

[56] References Cited

U.S. PATENT DOCUMENTS

| | | | |
|---|---|---|---|
| 4,048,111 | 9/1977 | Rosback et al. | 502/79 |
| 4,402,832 | 9/1983 | Gerhold | 210/659 |
| 4,440,871 | 4/1984 | Lok et al. | 502/214 |
| 4,503,282 | 3/1985 | Sikkenga | 585/671 |
| 4,513,153 | 4/1985 | Sandrin | 568/697 |
| 4,581,474 | 4/1986 | Hutson, Jr. et al. | 568/697 |
| 4,695,560 | 9/1987 | Gattuso et al. | 502/222 |
| 4,734,540 | 3/1988 | Gattuso et al. | 585/274 |
| 4,758,419 | 7/1988 | Lok et al. | 423/306 |
| 4,778,943 | 10/1988 | Sun | 585/671 |
| 4,814,517 | 3/1989 | Trubac | 568/697 |
| 4,814,519 | 3/1989 | Harandi et al. | 586/697 |
| 5,008,466 | 4/1991 | Schleppinghoff et al. | 568/697 |
| 5,157,178 | 10/1992 | Gajda et al. | 568/697 |
| 5,210,327 | 5/1993 | Luebke et al. | 568/697 |

Primary Examiner—Howard T. Mars
Attorney, Agent, or Firm—Thomas K. McBride; John G. Tolomei

[57] ABSTRACT

A combination of an etherification process and a process for the isomerization of linear alkenes to isoalkenes uses an adsorptive separation zone that receives an effluent fraction from the etherification reaction zone and separates the fraction at low efficiency to produce an isomerization feed stream comprising normal butenes and butanes, and a butane stream that is rejected from the process. The rejection of butanes at low efficiency reduces or eliminates the loss of butenes with the rejection of butane. A low efficiency adsorptive separation to reject butanes also benefits the isomerization process by inhibiting coking.

12 Claims, 1 Drawing Sheet

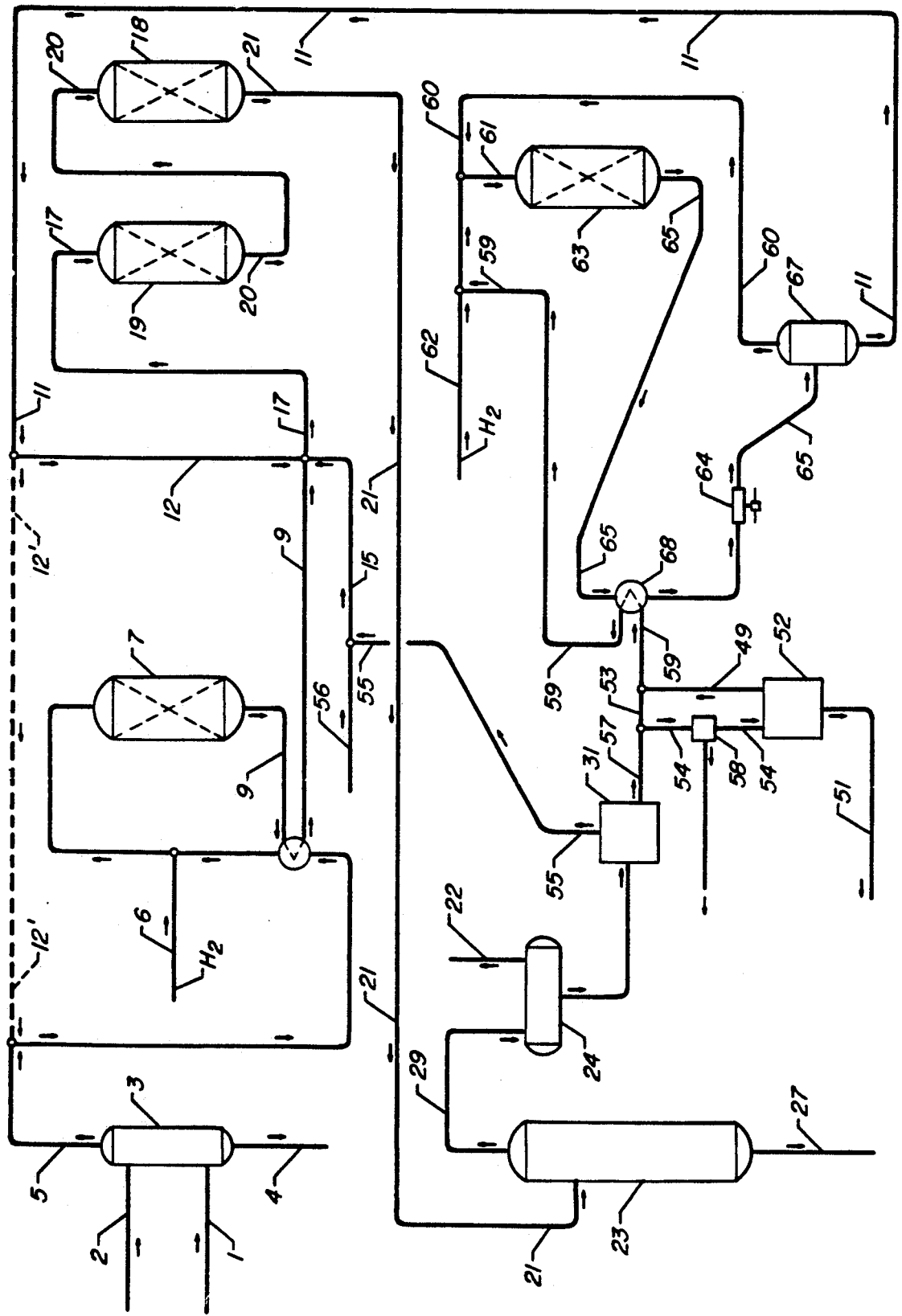

C4 REJECTION FOR ETHERIFICATION AND ISOMERIZATION PROCESS

FIELD OF THE INVENTION

This invention relates to processes for the production of ethers by the reaction of an alcohol with an isoolefin. More specifically this invention relates to a process for the production of ether and the skeletal isomerization of olefins to provide additional feedstock for the production of ethers and the rejection of unreactive butanes from the feed.

BACKGROUND OF THE INVENTION

The production of ethers by the reaction of an isoolefin and an alcohol are well known commercial operations. There are many detailed descriptions of processes for the production of such ethers, in particular, methyl tertiary butyl ether (MTBE) and tertiary amyl methyl ether (TAME). These ethers have long been known as useful octane blending agents for gasoline motor fuels due to their high octane number (RON) of about 120. More recently ether compounds as gasoline blending components have been highly valued as supplying oxygen to meet reformulated gasoline requirements. Processes for the production of MTBE and TAME by reacting methanol with isobutylene or isoamylene, respectfully, are among the most widely known processes for the production of such ethers.

Processes for the production of such ethers have suffered from a shortage of the necessary isoolefins for reaction with the alcohols to provide products. Feedstreams for etherification processes typically consist of a wide variety of olefinic and paraffinic isomers. It has been known to increase the available feedstock by the dehydrogenation of paraffins and the skeletal isomerization of olefins. Methods for the dehydrogenation of paraffins, in particular isoparaffins, are well known in the art as are processes for the skeletal isomerization of normal olefins to isoolefins. Since the olefinic and paraffinic isomers of any given carbon number have relatively close boiling points, separation of the isomers in an efficient manner to enhance the production of ether as well as the conversion of unreacted products to additional reactants have been difficult. It is particularly important to prevent the build up of saturated isomers since any purging of such isomers leads to a loss of olefin substrate. Methods for the various separations have included adsorptive separations as well as extractive distillations. There is a need for etherification and isomerization process arrangements that simplify the separation of olefinic and paraffinic isomers to provide product and reactants.

SUMMARY OF THE INVENTION

This invention is a combination of an etherification process and a process for the isomerization of linear alkenes to isoalkenes that uses an adsorptive separation zone to separate an effluent fraction from the etherification reaction zone and separates the fraction at low efficiency to produce an isomerization feed stream comprising normal butenes and butanes, and a butane stream that is rejected from the process. The rejection of butanes at low efficiency reduces or eliminates the loss of butenes with the rejection of butane. A low efficiency adsorptive separation to reject butanes also benefits the isomerization process by inhibiting coking in the isomerization zone. The use of the adsorptive separation zone can also be integrated with the isomerization zone and a selective hydrogenation zone for more efficient utilization of hydrogen.

Accordingly this invention in one embodiment is a process for the production of ethers from a feedstream of mixed $C_4$-$C_5$ saturated and unsaturated isomers and an alcohol. The process includes mixing at least a fraction of a feedstream comprising alkanes, normal alkenes and isoalkenes with a $C_1$-$C_5$ alcohol to produce a combined feed and contacting the combined feed with an etherification catalyst in an etherification zone at etherification conditions to react isoalkenes with the alcohol and produce an etherification effluent stream comprising, alcohol, alkyl ether, alkanes, and normal alkene isomers. The process passes a separation zone input stream comprising at least a portion of the etherification effluent stream to a first separation zone, withdrawing a high boiling first fraction comprising alkyl ether from the separation zone, and a second fraction comprising alcohol, alkanes, normal alkene isomers. Following recovery of alcohol from the second fraction, the process passes an adsorption feed comprising at least a portion of the second fraction to an adsorptive separation zone, contacts the adsorption feed with an adsorbent at adsorption conditions to separate the adsorption feed into a saturate stream comprising alkane isomers and an isomerization zone feed comprising normal alkenes and alkanes at a lesser concentration that the normal alkenes. The isomerization zone feed enters an isomerization reaction zone for the skeletal isomerization of normal alkenes that contacts the isomerization zone feed with an isomerization catalyst at isomerization conditions. At least a portion of an isomerization zone effluent stream withdrawn from said isomerization zone comprises isoalkene and passes to the etherification reaction zone to provide at least a portion of the etherification reaction zone feedstream. The feed stream enters the process loop by passing into at least one of the etherification zone, the separation zone and the isomerization zone.

Accordingly this invention in a more limited embodiment is a process for the production of butyl ethers from a mixed $C_4$ feedstream comprising butanes, normal butenes, and isobutene, and a monohydroxy alcohol. The process includes mixing at least a fraction of a feedstream comprising butanes, normal butenes and isobutene with a $C_1$-$C_5$ monohydroxy alcohol to produce a combined feed and contacting the combined feed with an etherification catalyst in an etherification zone at etherification conditions to react isobutene with the alcohol and produce an etherification effluent stream comprising, alcohol, butyl ether, butanes, and normal butene isomers. The process passes a separation zone input stream comprising at least a portion of the etherification effluent stream to a first separation zone, withdrawing a high boiling first fraction comprising the ether from the separation zone, and a second fraction comprising alcohol, butanes, normal butene isomers. Following recovery of alcohol from the second fraction, the process passes an adsorption feed comprising at least a portion of the second fraction to an adsorptive separation zone, contacts the adsorption feed with an adsorbent at adsorption conditions to separate the adsorption feed into a saturate stream comprising butane isomers and an isomerization zone feed comprising normal butenes and butane at a lesser concentration than the normal butenes. The isomerization zone feed enters an isomerization reaction zone for the skeletal isomerization of normal butenes that contacts the isomerization zone feed with an isomerization catalyst at isomerization conditions. At least a portion of an isomerization zone effluent stream withdrawn from said isomerization zone comprises isobutene and passes to the etherification reaction zone to provide at least a portion of the etherification reaction zone feedstream. The feed stream enters the process loop by passing into at least one of the etherification zone, the separation zone and the isomerization zone.

This invention can be applied to any feed containing saturated and unsaturated hydrocarbon isomers. Butane feedstocks derived from FCC units can be usefully processed in this invention. However, greatest advantage is obtained from this invention when using feeds having a high percentage of olefins. In preferred feeds the saturated butane isomers comprises from 5 to 90 wt % of the feedstream. Particularly preferred feedstreams are derived from steam cracker stream and have 80 wt % and higher olefin contents.

Additional aspects of this invention relate to the arrangements required for distillation of feedstreams, reaction zone locations and treatment zones. In particular, another aspect of this invention is the use of an adsorptive separation zone having selectivity for butene isomers and the reaction of unsaturated $C_4$ hydrocarbon isomers to produce MTBE. In another aspect of this invention the separation zone for the recovery of ether products may also provide reactive distillation to enhance the conversion of the product and the recovery of potential reactants. The following detailed description of the invention sets forth additional details, embodiments, and aspects of the invention.

BRIEF DESCRIPTION OF THE DRAWING

The Figure shows a schematic illustration of a process of this invention showing the etherification zone, isomerization zone, and adsorptive separation zone along with additional separators, and treating zones for the purification of the feedstream and product.

DETAILED DESCRIPTION OF THE INVENTION

This invention is broadly applicable to the production of a wide variety of ethers from a number of different feedstocks. The primary ethers for which this invention will be applied are tertiary, amyl and butyl ethers. The advantages of this invention are achieved when the feedstream includes a mixture of normal and branched alkene and alkane isomers. Where the etherification process is one for the production of butyl ethers, the typical feedstream will consist of a mixture of $C_4$ isomers comprising isobutane, isobutene, normal butane, 1-butene and 2-butene. Where the process is one for the production of amyl ethers, the feedstream components will include 3,methyl-1-butene, isopentane, 1-pentene, 2,methyl-1-butene, normal pentane, trans-2-pentene, cis-2-pentene and 2,methyl-2-butene in a typical distribution of isomers. Since in the combination of etherification and skeletal olefin isomerization processes, the alkanes are not reacted to any significant degree, these components increase the amount of material that passes through the process and must be removed to prevent an unacceptable build-up of unreacted products that circulate through the process. Although a variety of sources are available to provide such feedstreams, the most common source of the feedstreams for these processes are the previously mentioned light cracked hydrocarbon steams from an FCC unit, or a $C_4$ stream from a steam cracker after butadiene extraction.

Often these hydrocarbon streams will contain diolefins in addition to the desired monoolefin feed components. These diolefins interfere with the operation of the catalyst in downstream processes by polymerizing and forming heavy hydrocarbon compounds that block the active sites of the catalyst and prevent their use. Preferably, feedstreams for this process will undergo treatment for the elimination of diolefins. A common method of eliminating diolefins is by the selective hydrogenation of the diolefins to saturate the diolefins into monoolefins while preserving monoolefins. Those skilled in the art know a variety of selective hydrogenation processes for the saturation of diolefins to monoolefins. A particular catalyst and operating conditions for such selective hydrogenation processes can be found in U.S. Pat. Nos. 4,695,560 and 4,734,540 the contents of which are hereby incorporated by reference. The selective hydrogenation process typically employs a nickel on aluminum catalyst or a noble metal, such as palladium on alumina, for the selective hydrogenation. The nickel may be sulfided or unsulfided. The process can also operate at a broad range of operating conditions including pressures of from 40 to 800 psig with pressures of between 50 and 300 psig being preferred and temperatures of from 70°-700° F. with temperatures of from about 120°-400° F. being preferred. Effective space velocities for the processes should be above 1 $hr^{-1}$ and preferably are above 5 with a range of from between 1 to 35 $hrs^{-1}$. It is typical in such processes to limit the amount of hydrogen to prevent the saturation of monoolefins such that there is less than 2 times the stoichiometric amount of hydrogen required for the selective hydrogenation in the process. Preferably, the mol ratio of hydrogen to diolefinic hydrocarbons in the material will be in a range of from 1:1 to 1.8:1, and in some cases the hydrogen will be less than stoichiometrically required amount of hydrogen. Additional information related to the selective hydrogenation of diolefinic hydrocarbons, and in particular, unconjugated diolefinic hydrocarbons, can be found in the referenced patents.

The feed to the process includes an alcohol to react with the isoolefin and produce the desired ether product. The alcohols that can be used are typically $C_1$-$C_5$ monohydroxy alcohols. Methanol typically constitutes the alcohol of choice for the etherification process. Ethanol, although used less commonly, is also a commonly available alcohol for the etherification process. Methanol is preferred somewhat since it is a stable commercial chemical of long standing.

The isoalkene as well as the normal alkene hydrocarbons will enter the etherification zone along with the alcohol. Contact with the etherification catalyst at etherification conditions will produce the ether product. A wide range of materials are known to be effective as etherification catalysts for the isoalkene reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the art and include copolymers of sulfonyl fluorovinyl ether and fluorocarbons as described in U.S. Pat. No. 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 $m^2/g$, a pore volume of 0.6–2.5 ml/g and a mean pore diameter of 40–1000 angstroms. It is contemplated that the subject process could be performed using a metal-containing resin which contains one or more metals from sub-groups VI, VII or VIII of the Periodic Table such as chromium, tungsten, palladium, nickel, platinum, or iron as described in U.S. Pat. No. 4,330,679. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions.

The range of etherification conditions for processes operating in liquid phase still includes a broad range of suitable conditions including a superatmospheric pressure sufficient to maintain the reactants as a liquid phase, generally below about 700 psig, and a temperature between about 85 and about 210° F. Even in the presence of additional light materials, pressures in the range of 140 to 580 psig are sufficient. A preferred temperature range is from 100°–210° F. The reaction rate is normally faster at higher temperatures but conversion is more complete at lower temperatures due to favorable thermodynamic equilibrium. High conversion in a moderate volume reaction zone can, therefore, be obtained if the initial section of the reaction zone, e.g., the first two-thirds, is maintained above 160° F. and the remainder of the reaction zone is maintained below 120° F. This may be accomplished most easily with two reactors. The ratio of feed alcohol to isoolefin should normally be maintained in the broad range of 1:1 to 2:1. With the isobutene and isopentene reactants, good results are achieved if the ratio of methanol to isobutene is between 1.05:1 and 1.5:1. An excess of methanol, above that required to achieve satisfactory conversion at good selectivity, should be avoided as some decomposition of methanol to dimethyl ether may occur which may increase the load on separation facilities. Various etherification process techniques, reaction conditions and product recovery methods are described in U.S. Pat. Nos. 4,219,678 to Obenaus et al. and 4,282,389 to Droste et al. which are incorporated herein by reference.

The etherification zone operates selectively to principally convert only the isoolefins. Etherification zones normally obtain high isoalkene conversions which for $C_5$ hydrocarbons will usually exceed 95% and $C_4$ hydrocarbons will typically exceed 98%. Therefore, alkanes and normal alkenes pass through the etherification zone without any significant conversion to products or by-products. Thus, the etherification zone effluent together with the unreacted feed components provides a stream of ether product and normal and branched alkenes and alkane isomers for separation. In most cases, the stream entering the separation zone will also contain unreacted alcohol. The separation zone receiving the ether products, alcohol and unreacted hydrocarbons distills the product into three separate boiling point fractions. Similar to most separation systems for recovery of ethers, the product separation zone provides a high boiling fraction that principally contains ether product. The product separation zone of this invention separates the remaining lower boiling components into a low boiling fraction containing isoalkane, normal alkenes, and normal alkanes that were not reacted in the etherification process or enter the separation zone directly as part of the process feed.

Isoparaffins typically provide the lowest boiling constituent of the alkene and alkane isomers. While the isoalkanes can be conveniently withdrawn as a low boiling fraction from the separation zone, the purging of the isoalkane material results in the loss of valuable alkene materials or high capital and utility costs for a high recovery fractionation section. In a continuously circulating process of this invention, the normal alkanes must also find a path out of the process loop in order to prevent their build-up. Typically, past process arrangements withdrew a portion of the normal alkanes with the low boiling fraction from the separation zone. Withdrawal of the normal alkanes with the low boiling fraction establishes an equilibrium concentration of normal alkanes. The normal alkanes were purged from the process with the accompanying alkenes, since the normal alkene and alkane hydrocarbons present were usually suitable gasoline components. This invention eliminates the purge normal alkanes from the ether separation zone such that the alkanes corresponding in carbon number to the lowest boiling isoalkene reactant will have a concentration of less than 0.05 wt % in any vented light gas stream.

Following venting of light gases it is also normal practice to recover alcohol from the etherification effluent. Those skilled in the art are familiar with the various azeotropes formed by the ether products and alcohol and can provide suitable means for such separations and recoveries. As anticipated for most cases, methanol will be the usual alcohol and the alkene and alkane containing fraction will undergo an alcohol recovery step. Water washing provides the usual means for recovering methanol in such arrangements. In addition to ether separation the alkane and isoalkane fraction will ordinarily undergo oxygenates removal.

Following etherification and oxygenate separation, the alkane and alkene containing stream passes through a selective adsorption zone for the removal of a portion of the alkane isomers. The adsorptive separation zone can use any adsorbent and bed operating arrangement that will selectively adsorb the saturated or unsaturated isomers in a continuous system and provide high purity saturated hydrocarbon fraction containing less than about 2 vol % olefins and a low purity unsaturated hydrocarbon stream containing at least about 15 vol % paraffins. Suitable methods for the selective adsorption include swing bed systems and simulated moving bed system. Particular arrangements for moving bed systems are disclosed in U.S. Pat. Nos. 2,985,589 issued to Broughton, and 4,402,832 issued to Gerhold the contents of which are herein incorporated by reference.

A number of adsorbents are known for separating olefins from saturated hydrocarbons. Appropriate adsorbents are those made using zeolites that belong in the faujasite family and have been suitably cation exchanged. Sodium exchanged X and Y type zeolites are known to be useful in the separation of olefins from paraffinic hydrocarbons. Particular methods of treating type X and Y zeolites to improve olefin selectivity and reduce undesired cracking reactions are taught in U.S. Pat. No. 4,048,111 the teachings of which are herein incorporated by reference.

Although both liquid and vapor phase operations can be used in many adsorptive type separation processes, liquid-phase operation is preferred for this process because of the lower temperature requirements and because of the higher yields of adsorbed material or extract that can be obtained with liquid-phase operation over those obtained with vapor-phase operation. Adsorption conditions will, therefore, include a pressure sufficient to maintain liquid phase. Temperatures for the adsorption step of the separation will usually range from ambient to about 300° F. and pressure will range from atmospheric to 500 psig. Desorption conditions will generally include the same range of temperatures and pressures as used for extract conditions.

This process is especially suited for adsorption systems that use multiple beds for supplying the process streams to the adsorbent and divide the adsorbent into a plurality of zones for adsorbing olefins, recovering paraffins, purifying the adsorbent, and desorbing the olefins. A well-known process of this type is the simulated countercurrent moving bed system for simulating moving bed countercurrent flow systems and is generally taught in U.S. Pat. No. 3,510,423, the contents of which are hereby incorporated by reference. Such systems have a much greater separation efficiency than fixed molecular sieve bed systems. In the moving bed or simulated moving bed processes, the retention and displacement operations are continuously taking place which allows both continuous production of an extract and a raffinate stream and the continual use of feed and desorbent streams. In such a system it is the progressive movement of multiple liquid access points down a molecular sieve chamber that simulates the upward movement of molecular sieve contained in the chamber.

A number of specially defined terms are used in describing the simulated moving bed processes. The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In the preferred separation zone of this invention olefinic hydrocarbons from the feed stream are extract components while feed stream saturated or paraffinic components are raffinate components. The term "extract component" as used herein refers to a more selectively retained compound such as olefinic hydrocarbons in this process. The term "displacement fluid" "or desorbent" shall mean generally a material capable of displacing an extract component. The term "desorbent" or "desorbent input stream" indicates the stream through which desorbent passes to the molecular sieve. The term "raffinate output stream" means a stream through which most of the raffinate components are removed from the molecular sieve. The composition of the raffinate stream can vary from about 100% desorbent to essentially 100% raffinate components. The term "extract stream" or "extract output stream" means a stream through which an extract material which has been displaced by a desorbent is removed from the molecular sieve. The composition of the extract stream can also vary from about 100% desorbent to essentially 100% extract components.

The term "selective pore volume" of the molecular sieve is defined as the volume of the molecular sieve which selectively retains extract components from the feedstock. The term "non-selective void volume" of the molecular sieve is the volume of the molecular sieve which does not selectively retain extract components from the feedstock. This non-selective void volume includes the cavities of the molecular sieve which are not capable of retaining extract components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in non-selective void volume of the molecular sieve, it, in most instances, comprises less selectively retained feed components.

In the preferred simulated moving bed process only four of the access lines are active at any one time: the feed input stream, displacement or desorbent fluid inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves liquid through different zones which require different flow rates. A programmed flow controller may be provided to set and regulate these flow rates.

The active liquid access points effectively divide the molecular sieve chamber into separate zones, each of which has a different function. In this embodiment of the process, it is generally necessary that three separate operational zones be present in order for the process to take place although in some instances an optional fourth zone may be used.

The retention or extraction zone, zone 1, is defined as the molecular sieve located between the feed inlet stream and the raffinate outlet stream. In this zone, the feedstock contacts the molecular sieve, an extract component is retained, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the molecular sieve between the extract outlet stream and the feed inlet stream. The basic operations taking place in zone 2 are the displacement from the non-selective void volume of the molecular sieve of any raffinate material carried into zone 2 by the shifting of molecular sieve into this zone and the displacement of any raffinate material retained within the selective pore volume of the molecular sieve. Purification is achieved by passing a portion of extract stream material leaving zone 3 into zone 2 at zone 2's upstream boundary to effect the displacement of raffinate material. The flow of material in zone 2 is in a downstream direction from the extract outlet stream to the feed inlet stream.

Immediately upstream of zone 2 with respect to the fluid flowing in zone 2 is the displacement or desorption zone, zone 3. The desorption zone is defined as the molecular sieve between the desorption inlet and the extract outlet stream. The function of the desorption zone is to allow a desorbent which passes into this zone to displace the extract component which was retained in the molecular sieve during a previous contact with feed in zone 1 in a prior cycle of operation. The flow of fluid in zone 3 is essentially in the same direction as that of zones 1 and 2.

In some instances, an optional buffer zone, zone 4, has been utilized. This zone, defined as the molecular sieve between the raffinate outlet stream and the desorbent inlet stream, if used, is located immediately upstream with respect to the fluid flow to zone 3. Since this invention purposefully operates at a low efficiency to maintain paraffins in the extract stream zone 4 is not usually necessary. Therefore, the raffinate stream passed from zone 1 to zone 3 does not need careful monitoring since an appreciable quantity of raffinate material can contaminate the extract stream.

A cyclic advancement of the input and output streams through the fixed bed of molecular sieve can be accomplished by utilizing a manifold system in which the valves in the manifold are operated in a sequential manner to effect the shifting of the input and output streams thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, displacement fluid input and raffinate output streams pass are advanced in the same direction as fluid flow through the molecular sieve bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In liquid phase adsorption systems the adsorbent contains selective pores that will more strongly adsorb the selectively adsorbed components in the feed mixture. Most moving bed adsorption processes use a desorbent material that has a different composition than the primary components in the feed stream to the adsorption section to displace extract materials from the selective pore volume. Therefore, both the extracted and rejected feed mixture components are recovered from the adsorption section in admixture with the desorbent components. It is economical to recover the desorbent material from the material from these streams for reuse in the adsorption section. It has been the usual practice to use a raffinate column to separate the desorbent material from the raffinate stream and an extract column is typically used to recover desorbent from the extract stream.

A useful desorbent for the typical feedstream of this invention will comprise a saturated and unsaturated mixture of aliphatic hydrocarbons having a higher carbon number than the feed stream hydrocarbons. The higher carbon number desorbents are readily separated by fractionation from the separated feedstream components. For example, in the case butene and butane separation a preferred desorbent mixture comprises a mixture of normal hexane and normal hexene. Preferably the mixture comprises 30 to 70% hexenes.

Due the advantages of having some concentration of saturated paraffins in the feed to the isomerization zone the adsorptive separation zone operates at relaxed design conditions. Minimum acceptable purities for the process of this invention are about 75%. Preferably the recovery of olefins will greater than 85%. The unrestrictive magnitude of these purities and recoveries permit the adsorptive zone to provide a raffinate stream for rejection and an extract stream for further processing in the isomerization zone of this invention.

By-passing a portion of the alkene and alkane stream around the adsorptive separation zone can provide further adjustments in the relative olefin to paraffin concentration of the feed stream to the isomerization zone. Where the paraffin concentration of the feedstream is high only a relative small portion of the unreacted etherification effluent need pass through the adsorptive separation zone for paraffins removal. The concentration of the paraffins maintained in the isomerization zone feed is preferably in a range of from 1 to 20 wt %. Thus the amount of unreacted etherification effluent bypassing the adsorptive separation zone can vary from 0 to 20 vol %.

Whether all or a portion undergo adsorption, the unreacted alkene and alkane from the etherification zone undergo skeletal isomerization of the normal alkenes to produce additional isoalkenes for the etherification process. In order to maintain catalyst stability in the isomerization zone the streams entering the isomerization zone often requires removal of polar contaminants such as sulfur, nitrogen or oxygen compounds. Thus, in addition to processing for the recovery of methanol, unreacted etherification fraction may also require additional purification for the removal of compounds that can poisonous the catalyst or interfere with the skeletal isomerization process. Compounds that are usually most harmful to the isomerization catalyst include water, oxygenate compounds and nitrogen compounds. The water and oxygenate compounds suppress the isomerization catalyst activity. The nitrogen compounds also affect the isomerization catalyst activity and results in a reduced activity. These nitrogen compounds are also poison to acidic ion exchange resins used for the etherification and thus are also beneficially removed prior to the etherification. A variety of methods are known to remove such compounds which include water washing, adsorption and extraction processes. Oxygenate compounds and nitrogen compounds can be removed by typical adsorbents for the removal of these contaminants comprised zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such dimethyl ethers from the effluent from an etherification process is described in U.S. Pat. No. 4,814,517, the contents of which are hereby incorporated by reference. Suitable operation of the isomerization zone will require the removal of water and oxygenate compounds to a level of less than 50 wppm, and preferably less than 5 wppm water equivalents. Common nitrogen and oxygenate compounds that have also been found in light cracked products from an FCC unit include acetone and acetonitrile. These compounds are preferably removed by water washing such feeds prior to introduction into the process.

The normal alkene-rich input stream after purification enters the isomerization zone. (The term rich when used herein means a stream having a weight or volume percent content of at least 50% of the mentioned component while the term relatively rich means a stream having a higher concentration of the mentioned component than the feed from which it was derived.) When the process is used to produce MTBE the isomerization zone will usually contain at least 8 wt % butane. The coking benefit of this invention will be obtained by having from 1 to 50 wt % of the butanes in the feed.

Methods for converting the normal alkene components to isoalkene components by isomerization are well known in the art. A process for converting linear alkenes to isomerized alkenes using a crystalline or silicate molecular sieve is taught in U.S. Pat. No. 4,503,282. Additional catalyst and methods for the skeletal isomerization of linear alkenes are described in U.S. Pat. Nos. 4,778,943 and 4,814,519. A preferred catalyst for the isomerization reaction zone of this invention is a nonzeolitic molecular sieve. Preferred forms of the nonzeolitic molecular sieve for this invention includes silicoaluminophosphates and a magnesium aluminophosphate. Suitable non-zeolitic catalysts such as the SAPO and MgGAPO are described in U.S. Pat. Nos. 4,440,871 and 4,758,419 which are hereby incorporated by reference. The catalyst for the isomerization zone typically lies in a fixed bed arrangement. In order to permit in-situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01 to 9, and preferably in a ratio of from 1 to 7, aids the process by suppressing the formation of carbon compounds on the catalyst. The isomerization process will typically operate over a broad range of conditions including temperatures of from 120°-1300° F. with temperatures in the range of 200°-1000° F. being preferred. Pressures for the isomerization reaction will also vary over a wide range extending from atmospheric conditions to 700 psig, and preferably are in a range of 50 to 350 psig. Space velocities can also vary over a wide range from 0.5 to 100 hr$^{-1}$ with a preferred range of 1-5 hr$^{-1}$. The expected per pass conversion of normal alkenes to isoalkenes in the isomerization zone will generally reach at least 40% of the total combined feed entering the reaction zone and will more typically exceed 50%.

The effluent stream from the isomerization zone containing isoalkenes normally undergoes separation for the recovery of light gases including hydrogen. Hydrogen recovered in the light gases from the isomerization zone is recycled to the inlet of the isomerization zone to provide any necessary hydrogen concentration. The effluent from the isomerization zone may also undergo additional separation to remove additional light ends or reject heavier by-product hydrocarbons. Heavy materials such as $C_6+$ hydrocarbons tend to foul or deactivate the etherification catalyst. The presence of light ends in the isomerization zone effluent passes this light material on to the etherification zone as uncondensibles that, when rejected from the etherification separation system, drag methanol into downstream facilities thereby causing corrosion problems and methanol loss.

The isomerization zone may also operate without the separation of light ends for the recovery of hydrogen. In one embodiment the isomerization zone may operate with once through hydrogen addition which only adds hydrogen up to about the solubility limits of the isomerization feed. For once through operations the feed to the isomerization zone will usually have a hydrogen to hydrocarbon ratio of 0.1 to 1. It is also possible to operate the isomerization zone with no addition of hydrogen. A particularly preferred arrangement of this invention includes an selective hydrogenation reactor to saturate diolefins and the effluent from the isomerization zone is returned directly to the selective hydrogenation reactor without intermediate separation to supply the hydrogen for the selective hydrogenation.

In the simplest arrangement of this invention, the effluent from the isomerization zone, after any separation, is admixed with the feed to the etherification zone to provide additional isoalkene reactants. The return of the isomerization effluent to the etherification reaction provides a loop incorporating components that are recycled through the process. Preferably, the feedstream of mixed, branched, and normal alkenes and alkanes will enter the process at a point in the loop just ahead of the etherification reaction zone. However, this feedstream may be added at a number of different points, depending on its composition, within this loop. For example, it is also possible to add the feedstream at a point just ahead of the adsorptive separation zone. In this way the total flow of reactants through the etherification zone is reduced by eliminating non-reactive isoalkane hydrocarbons. Those skilled in the art are aware of the particular characteristics of the feedstream and the desired product streams that will dictate the most advantageous location for introducing the feedstream.

EXAMPLE

This invention is further described in the context of an example for the production of methyl tertiary butyl ether (MTBE) using a process or an arrangement as shown in the Figure. This example presents engineering calculations based on data from operating process units and laboratory test results. Relative flowing compositions for the major process streams of this Example are shown in the Table on a water-free basis. In this example, a feed comprising a $C_4$ cut from the product stream of a cracking unit enters the process through line 1 and passes through a water wash zone 3. Water entering water wash zone 3 by a line 2 removes soluble nitrogen compounds and light oxygenates from the feed through a line 4. Line 5 recovers the purified feed at a liquid flow of about 5419 barrels per day and passes the feed into admixture with a hydrogen stream 6 and then to a selective hydrogenation reactor 7 for the removal trace diolefin compounds. Line 9 carries the treated feed which is saturated with water and on a water-free basis has the relative flowing composition given in the Table. Line 9 after heat exchange with the incoming feed of line 5 in an exchanger 10, admixes the treated feed with 31201 barrels per day of a isobutene containing recycle stream carried by lines 11 and 12. Optionally a portion of the recycle stream carried by line 11 may be diverted by line 12' to supply hydrogen to the inlet of saturation reactor 7. Methanol in an amount of 525.6 lb-mol/hr carried by line 15 mixes with the combined pentane feed carried by line 15 to provide an etherification feedstream having the relative composition given in the Table and passed by line 17 into an etherification reactor 19. Etherification reactor 19 contacts the combined feed with a sulfonated solid resin catalyst at a temperature of about 170° and a pressure of about 88 psig. Catalyst in etherification reactor 19 is arranged as a solid bed. A line 20 carries the effluent from etherification reactor 19 to a second etherification reactor 18 operating in a similar manner as etherification reactor 19. Effluent from the second etherification reactor passes via a line 21 to a distillation column 23. The Table lists the relative composition of line 21. The contents of line 21 enters column 23 at an average temperature of about 170° F. and a pressure of 88 psig. A bottoms stream 27 carries the MTBE product from the column and has the relative composition given in the Table. An overhead stream 29 carries unreacted methanol and butenes and lighter hydrocarbons from column 23. A portion of the overhead carried by line 29 is cooled, condensed and refluxed (not shown) to the top of column 23 after separation of light gases by a line 22 from a receiver 24. Line 30 carries the remainder of the effluent to a methanol recovery zone 31 for the recovery of methanol via water washing. A line 55 carries methanol from the top of zone 31 and combines it with fresh methanol entering by a line 56 to provide the methanol for the etherification through line 15. Water washed hydrocarbons taken from methanol recovery zone 31 via line 57 and having the relative flowing composition given in the Table are split into an adsorption feed fraction which takes about 10 vol % by a line 54 and a bypass stream that carries the remainder by a line 53. Adsorption feed taken by line 54 passes through a water and oxygenate removal zone 58 for the withdrawal of trace amounts of oxygenates such as dimethyl ether and water. Treatment of stream 54 in zone 58 lowers the concentration of water and water equivalent in line 54 to less than 30 wppm.

The remaining contents of line 54 enter a simulated moving bed adsorptive separation zone 52. Adsorptive separation zone 52 contains an adsorbent capable of extracting unsaturated species and rejecting saturates that contacts the feed mixture at a temperature of about 180° F. and a pressure of about 250 psig in a four zone simulated moving bed adsorption system. The system cycles through eight separate beds that contain the adsorbent in a cycle time of about 20 minutes. A desorbent consisting of a mixture of normal hexane and hexene desorbs the adsorbed olefins to provide an extract column product having a purity of about 80% at a recovery rate of about 87% which is recovered by a line 49 having the composition given in the Table. A line 51 rejects the paraffin rich raffinate from the process.

The contents of line 53 are combined with the contents of line 49 to form a combined isomerization feed carried by line 59 into a admixture with a make hydrogen from line 62 a hydrogen recycle stream carried by a line 60. The combined hydrogen and hydrocarbons form a combined feed 61 that has the composition listed in the Table and enters a reactor 63 for the skeletal isomerization of normal pentens to isopentenes. The combined feed enters the isomerization reaction zone at a temperature of about 120° F. and pressure of about 290 psia. The combined feed contacts a silicoaluminophosphate catalyst of the SAPO-11 type within the reaction zone. Line 65 withdraws the product effluent from the isomerization reactor which, after cooling against the entering feed stream in an exchanger 68 and a cooler 64, passes through a liquid vapor separation zone 67. The liquid vapor separation zone recovers the hydrogen rich recycle stream 60. A line 71 transfers the heavier components from separator 67 to a line 11.

TABLE

| STREAM COMPOSITION - MOL % | | | | | | | |
|---|---|---|---|---|---|---|---|
| | Line 9 | Line 17 | Line 21 | Line 27 | Line 49 | Line 57 | Line 61 |
| $H_2$ | 0.25 | 0.17 | 0.17 | — | — | 0.16 | 0.16 |
| $C_1$–$C_3$ | — | 3.05 | 2.99 | — | — | 3.74 | 3.22 |
| isobutane | 31.92 | 50.16 | 49.20 | — | 10.0 | 53.45 | 53.41 |
| isobutene | 14.41 | 7.77 | — | — | 0.02 | 0.01 | 0.01 |
| 1-Butene | 4.80 | 2.34 | 2.99 | — | 8.91 | 2.49 | 2.71 |
| Normal Butane | 10.18 | 17.54 | 17.20 | — | 10.00 | 18.69 | 18.85 |
| Trans-2-Butene | 19.22 | 9.34 | 9.16 | 0.12 | 35.54 | 9.94 | 10.82 |
| Cis-2-Butene | 19.22 | 9.34 | 9.16 | 0.12 | 35.54 | 9.94 | 10.82 |
| Butadiene | — | — | — | — | — | — | — |
| $C_5$'s | — | 0.31 | 0.30 | 3.83 | — | — | — |
| $C_6$+ | — | — | — | — | — | — | — |
| $H_2O$ wppm | — | — | — | — | — | — | — |
| Methanol | — | — | 1.91 | — | — | 2.08 | — |
| MTBE | — | — | 7.61 | 95.94 | — | — | — |

What is claimed is:

1. A process for the production of methyl tertiary butyl ether (MTBE) from a mixed $C_4$ feedstream comprising butanes, normal butenes, and isobutene, and methanol, said process comprising:

(a) mixing at least a fraction of a feedstream comprising butanes, normal butenes and isobutene with methanol to produce a combined feed and contacting said combined feed with an etherification catalyst in an etherification zone at etherification conditions to react isobutene with said methanol and produce an etherification effluent stream comprising, methanol, MTBE, butanes, and normal butene isomers;

(b) passing a separation zone input stream comprising at least a portion of said etherification effluent stream to a first separation zone, withdrawing a high boiling first fraction comprising said ether from said separation zone, and a second fraction comprising methanol, butanes, normal butene isomers;

(c) recovering methanol from said second fraction and passing an adsorption feed comprising at least a portion of said second fraction to an adsorptive separation zone, contacting said adsorption feed with an adsorbent at adsorption conditions to separate said adsorption feed into a saturate stream comprising butane isomers and an isomerization zone feed comprising normal butenes and butane at a lesser concentration than said normal butenes;

(d) passing said isomerization zone feed to an isomerization reaction zone for the skeletal isomerization of normal butenes and contacting said isomerization zone feed with an isomerization catalyst at isomerization conditions;

(e) withdrawing an isomerization zone effluent stream comprising isobutene from said isomerization zone and passing at least a portion of said isomerization zone effluent to said etherification reaction zone to provide at least a portion of said etherification reaction zone feedstream; and, (f) passing said feedstream into at least one of said etherification zone, said separation zone and said isomerization zone.

2. The process of claim 1 wherein a portion of said isomerization zone effluent enters a second separation zone and said second separation zone produces an overhead stream comprising $C_4$ and lighter hydrocarbon gases, a bottom stream comprising $C_8$ and higher boiling hydrocarbons and an intermediate stream comprising isobutene and normal butane.

3. The process of claim 1 wherein said adsorption feed passes through an oxygenate removal zone for the separation of oxygenate compounds before entering said adsorptive separation zone.

4. The process of claim 1 wherein said adsorbent selectively adsorbs butenes and isobutene.

5. The process of claim 1 wherein said adsorption zone operates at a temperature of from 120° F. to 240° F. and a pressure of 150 psig and 400 psig.

6. The process of claim 1 wherein said isomerization zone feed has a butane concentration of at least 1 mol % and said feed enters said isomerization zone at a hydrogen to hydrocarbon ratio of less than 20.

7. The process of claim 1 wherein at least one of said fraction of said feedstream and separation zone input stream passes through a selective hydrogenation zone and contacts a selective hydrogenation catalyst at selective hydrogenation conditions to saturate diolefins.

8. The process of claim 1 wherein said feedstream contains at least 80 wt % butenes.

9. The process of claim 1 wherein said adsorption feed comprises from 10 to 90 wt % of said second fraction.

10. The process of claim 9 wherein said isomerization zone feed includes a portion of said second fraction that by-passes said adsorption zone.

11. The process of claim 10 wherein a portion of said isomerization zone effluent stream passes directly from said isomerization zone to said selective hydrogenation zone without intermediate separation.

12. The process of claim 11 wherein said portion of said isomerization effluent stream supplies all of the hydrogen for said selective hydrogenation zone.

* * * * *